(12) United States Patent
Edwards et al.

(10) Patent No.: US 11,534,343 B2
(45) Date of Patent: Dec. 27, 2022

(54) DEVICES AND METHODS FOR PREVENTING LOCALIZED PRESSURE POINTS IN DISTRIBUTION COMPONENTS FOR TISSUE THERAPY

(71) Applicant: KCI Licensing, Inc., San Antonio, TX (US)

(72) Inventors: Thomas Alan Edwards, Southampton (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 638 days.

(21) Appl. No.: 16/449,750

(22) Filed: Jun. 24, 2019

(65) Prior Publication Data
US 2020/0038250 A1 Feb. 6, 2020

Related U.S. Application Data

(60) Provisional application No. 62/712,601, filed on Jul. 31, 2018.

(51) Int. Cl.
*A61F 13/02* (2006.01)
*A61F 13/00* (2006.01)

(52) U.S. Cl.
CPC .... *A61F 13/0216* (2013.01); *A61F 13/00068* (2013.01); *A61F 13/0253* (2013.01);
(Continued)

(58) Field of Classification Search
CPC .............. A61M 1/0086; A61M 3/0279; A61M 39/105; A61M 1/0084; A61M 1/0088;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report and Written Opinion for Corresponding Application No. PCT/US2019/038684, dated May 27, 2020.
(Continued)

*Primary Examiner* — Philip R Wiest
*Assistant Examiner* — Alessandro R Del Priore

(57) ABSTRACT

Apparatuses and dressing components for tissue treatment with negative pressure and methods of making and using the dressings and dressing components are disclosed. For example, an apparatus for managing fluid from a tissue site may comprise at least two fluid pathways formed along the length of the apparatus. The apparatus may have at least one hinge line spanning along the length of the apparatus between at the at least two fluid pathways, and the apparatus may be curved about the hinge line. Some examples of the apparatus may comprise multiple layers assembled in a stacked relationship, which may be bonded together using weld lines to define at least two fluid pathways along the length of the apparatus. In some examples, the apparatus may be curved about the weld lines.

10 Claims, 10 Drawing Sheets

(52) U.S. Cl.
CPC .............. *A61F 2013/0028* (2013.01); *A61F 2013/00174* (2013.01)

(58) Field of Classification Search
CPC ... A61M 39/00; A61M 1/90; A61F 13/00068; A61F 13/0216; A61F 13/0253; A61F 2013/00174; A61F 2013/0028; A61P 17/02
See application file for complete search history.

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2010/0160877 A1* | 6/2010 | Kagan ............... A61F 13/0203 604/319 |
| 2011/0184362 A1* | 7/2011 | Croizat ................ A61M 1/90 604/319 |
| 2013/0123722 A1 | 5/2013 | Pratt et al. |
| 2013/0144230 A1* | 6/2013 | Wu .................. A61F 13/0216 604/319 |
| 2014/0163491 A1 | 6/2014 | Schuessler et al. |
| 2015/0080788 A1 | 3/2015 | Blott et al. |
| 2016/0106892 A1* | 4/2016 | Hartwell ............. A61M 1/86 604/304 |
| 2018/0361038 A1* | 12/2018 | Croizat ............... A61M 1/90 |
| 2019/0321232 A1* | 10/2019 | Jardret ............ A61F 13/0216 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |

(56) References Cited

FOREIGN PATENT DOCUMENTS

| EP | 0117632 | A2 | 9/1984 |
|---|---|---|---|
| EP | 0161865 | A2 | 11/1985 |
| EP | 0358302 | A2 | 3/1990 |
| EP | 1018967 | A1 | 7/2000 |
| GB | 692578 | A | 6/1953 |
| GB | 2 195 255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 333 965 | A | 8/1999 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 93/009727 | A1 | 5/1993 |
| WO | 94/20041 | A1 | 9/1994 |
| WO | 96/05873 | A1 | 2/1996 |
| WO | 97/18007 | A1 | 5/1997 |
| WO | 99/13793 | A1 | 3/1999 |
| WO | 2016126444 | A1 | 8/2016 |
| WO | 2017119996 | A1 | 7/2017 |
| WO | 2019084006 | A1 | 5/2019 |
| WO | 2020040960 | A1 | 2/2020 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
European Examination Report Corresponding to Application No. 198520033, dated Jun. 2, 2022.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

\* cited by examiner

DEVICES AND METHODS FOR PREVENTING LOCALIZED PRESSURE POINTS IN DISTRIBUTION COMPONENTS FOR TISSUE THERAPY

RELATED APPLICATIONS

The present application claims the benefit, under 35 USC § 119(e), of the filing of U.S. Provisional Patent Application Ser. No. 62/712,601, entitled "Devices and Methods for Preventing Localized Pressure Points in Distribution Components for Tissue Therapy," filed Jul. 31, 2018, which is incorporated herein by reference for all purposes.

TECHNICAL FIELD

The invention set forth in the appended claims relates generally to tissue treatment systems and more particularly, but without limitation, to dressings and other distribution components for tissue treatment with negative pressure and methods of using the dressings and other distribution components for tissue treatment with negative pressure.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, an apparatus for managing fluid from a tissue site may include a first fluid pathway formed along a length of the apparatus, a second fluid pathway formed along the length of the apparatus, and a third fluid pathway formed along the length of the apparatus. The first fluid pathway may include a first plurality of bubbles. The apparatus may further include a first hinge line spanning along the length of the apparatus between the second fluid pathway and the third fluid pathway, and the apparatus may be curved about the first hinge line. In some embodiments, the first plurality of bubbles comprises a plurality of blisters.

In some additional embodiments, an apparatus for managing fluid from a tissue site may include a first layer comprising a first polymeric film and a first plurality of bubbles extending from a surface of the first layer, and a second layer comprising a second polymeric film, wherein the second layer is coupled to the first layer to cover the first plurality of bubbles and to form a sealed space between the first layer and the second layer. The apparatus may further include a first barrier and a second barrier coupled between the first layer and the second layer. The first barrier and the second barrier may define a first fluid pathway in the sealed space between the first barrier and the second barrier, a second fluid pathway in the sealed space between the first barrier and a first seal formed between a first portion of the first layer and a first portion of the second layer, and a third fluid pathway in the sealed space between the second barrier and a second seal formed between a second portion of the first layer and a second portion of the second layer. The second fluid pathway and the third fluid pathway may be outboard of a first hinge line spanning along a length of the sealed space between the second fluid pathway and the third fluid pathway, and the apparatus is curved about the first hinge line.

In further embodiments, an apparatus for managing fluid from a tissue site may include a first layer comprising a first polymeric film having a first side and a second side and a first plurality of bubbles extending from a first side of the first layer. The apparatus may further include a second layer comprising a second polymeric film having a first side and a second side, wherein the second layer may be adapted to be coupled to the first side of the first layer to cover the first plurality of bubbles and to form a sealed space between the first layer and the second layer. The apparatus may also include a third layer and a fourth layer. The third layer may comprise a third polymeric film and a first port, and the third layer may be adapted to be positioned against a second side of the first layer. The fourth layer may comprise a fourth polymeric film and a second port, and the fourth layer may be adapted to be positioned against a first side of the second layer. The apparatus may have a length and a width, and may further include a first section, a second section, and a third section across the width, wherein the first section comprises a flat face and the second section and the third section are each adapted to curve away from the flat face.

In still further embodiments, a method of assembling an apparatus for managing fluid from a tissue site may include providing a first layer comprising a first polymeric film and a first plurality of bubbles extending from a first surface of the first layer. The method may further include placing a second layer comprising a second polymeric film adjacent to the first surface of the first layer, positioning a third layer comprising a third polymeric film adjacent to a second surface of the first layer, and placing a fourth layer comprising a fourth polymeric film adjacent to a first surface of the second layer. The method may further include bonding the first layer, the second layer, the third layer, and the fourth layer together along a bond line to define a first fluid pathway, a second fluid pathway, and a third fluid pathway, wherein the bonding creates a curvature across a width of at least a portion of the apparatus.

Objectives, advantages, and a preferred mode of making and using the claimed subject matter may be understood best

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
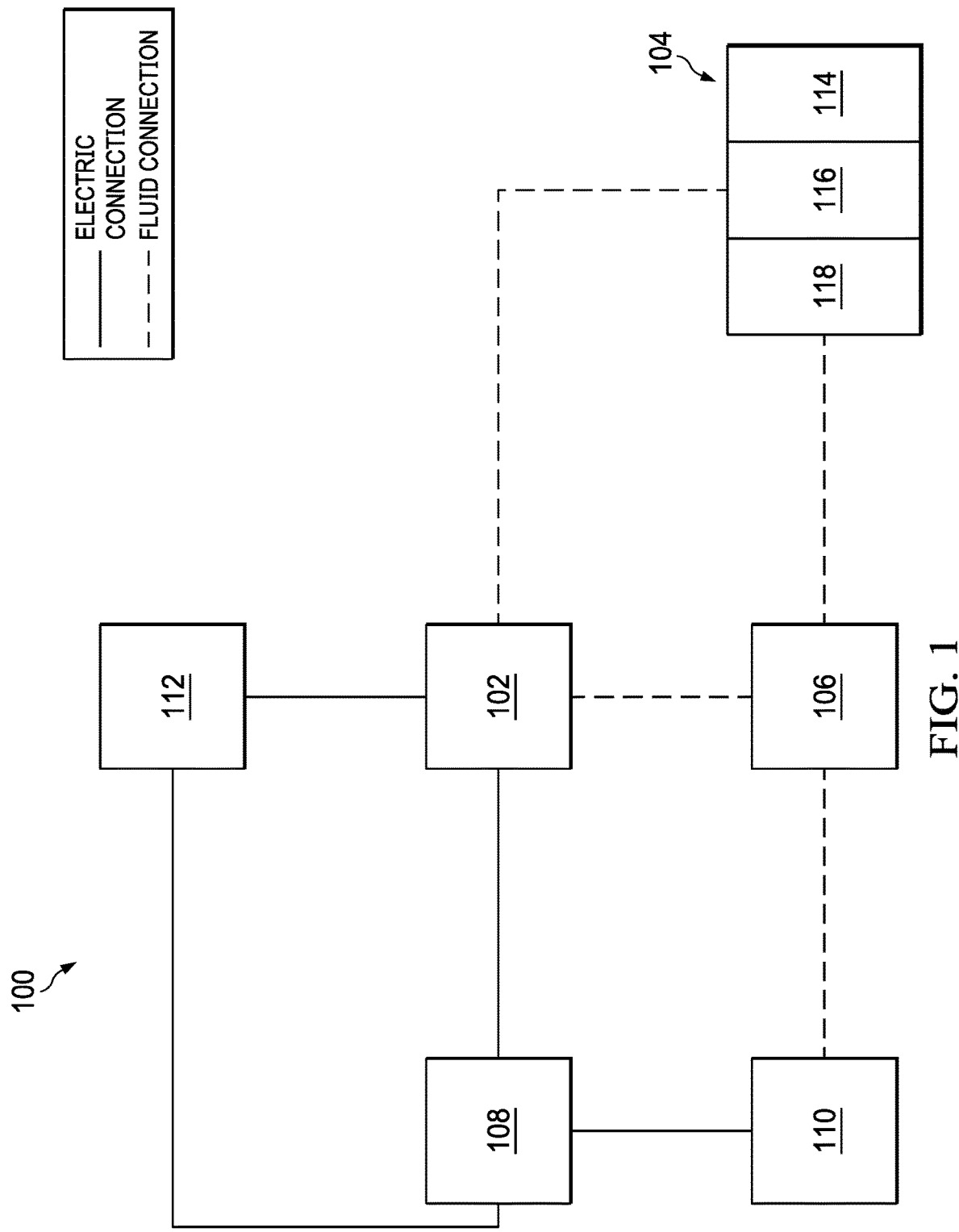
FIG. 1 is a functional block diagram of an example embodiment of a therapy system that can provide negative-pressure treatment in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 102, and one or more distribution components. A distribution component is preferably detachable and may be disposable, reusable, or recyclable. A dressing, such as a dressing 104, and a fluid container, such as a container 106, are examples of distribution components that may be associated with some examples of the therapy system 100. As illustrated in the example of FIG. 1, the dressing 104 may comprise or consist essentially of a tissue interface 114, a cover 116, a dressing interface 118, or combinations thereof in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 104. For example, such a dressing interface may be a SENSA-T.R.A.C.™ Pad available from Kinetic Concepts, Inc. of San Antonio, Tex.

The therapy system 100 may also include a regulator or controller, such as a controller 108. Additionally, the therapy system 100 may include sensors to measure operating parameters and provide feedback signals to the controller 108 indicative of the operating parameters. As illustrated in FIG. 1, for example, the therapy system 100 may include a first sensor 110 and a second sensor 112 coupled to the controller 108.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the controller 108 and other components into a therapy unit.

In general, components of the therapy system 100 may be coupled directly or indirectly. For example, the negative-pressure source 102 may be directly coupled to the container 106 and may be indirectly coupled to the dressing 104 through the container 106. Coupling may include fluid, mechanical, thermal, electrical, or chemical coupling (such as a chemical bond), or some combination of coupling in some contexts. For example, the negative-pressure source 102 may be electrically coupled to the controller 108 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 102, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 102 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 108, may be a microprocessor or computer programmed to operate one or more components of the therapy system 100, such as the negative-pressure source 102. In some embodiments, for example, the controller 108 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 114, for example. The controller 108 is also preferably configured to receive one or more input signals, such as a feedback signal, and programmed to modify one or more operating parameters based on the input signals.

Sensors, such as the first sensor 110 and the second sensor 112, are generally known in the art as any apparatus operable to detect or measure a physical phenomenon or property, and generally provide a signal indicative of the phenomenon or property that is detected or measured. For example, the first sensor 110 and the second sensor 112 may be configured to measure one or more operating parameters of the therapy system 100. In some embodiments, the first sensor 110 may be a transducer configured to measure pressure in a pneumatic pathway and convert the measurement to a signal indicative of the pressure measured. In some embodiments, for example, the first sensor 110 may be a piezo-resistive strain gauge. The second sensor 112 may optionally measure operating parameters of the negative-pressure source 102, such as a voltage or current, in some embodiments. Preferably, the signals from the first sensor 110 and the second sensor 112 are suitable as an input signal to the controller 108, but some signal conditioning may be appropriate in some embodiments. For example, the signal may need to be filtered or amplified before it can be processed by the controller 108. Typically, the signal is an electrical signal, but may be represented in other forms, such as an optical signal.

The tissue interface 114 can be generally adapted to partially or fully contact a tissue site. The tissue interface 114 may take many forms, and may have many sizes, shapes, or thicknesses, depending on a variety of factors, such as the type of treatment being implemented or the nature and size of a tissue site. For example, the size and shape of the tissue interface 114 may be adapted to the contours of deep and irregular shaped tissue sites. Any or all of the surfaces of the tissue interface 114 may have an uneven, coarse, or jagged profile.

In some embodiments, the tissue interface 114 may comprise or consist essentially of a manifold. A manifold in this context may comprise or consist essentially of a means for collecting or distributing fluid across the tissue interface 114 under pressure. For example, a manifold may be adapted to receive negative pressure from a source and distribute negative pressure through multiple apertures across the tissue interface 114, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 114 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 114 may also vary according to needs of a prescribed therapy. The 25% compression load deflection of the tissue interface 114 may be at least 0.35 pounds per square inch, and the 65% compression load deflection may be at least 0.43 pounds per square inch. In some embodiments, the tensile strength of the tissue interface 114 may be at least 10 pounds per square inch. The tissue interface 114 may have a tear strength of at least 2.5 pounds per inch. In some embodiments, the tissue interface may be foam comprised of polyols such as polyester or polyether, isocyanate such as toluene diisocyanate, and polymerization modifiers such as amines and tin compounds. In some examples, the tissue interface 114 may be reticulated polyurethane foam such as found in GRANUFOAM™ dressing or V.A.C. VERAFLO™ dressing, both available from Kinetic Concepts, Inc. of San Antonio, Tex.

The thickness of the tissue interface 114 may also vary according to needs of a prescribed therapy. For example, the thickness of the tissue interface may be decreased to reduce tension on peripheral tissue. The thickness of the tissue interface 114 can also affect the conformability of the tissue interface 114. In some embodiments, a thickness in a range of about 5 millimeters to 10 millimeters may be suitable.

The tissue interface 114 may be either hydrophobic or hydrophilic. In an example in which the tissue interface 114 may be hydrophilic, the tissue interface 114 may also wick fluid away from a tissue site, while continuing to distribute negative pressure to the tissue site. The wicking properties of the tissue interface 114 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

In some embodiments, the tissue interface 114 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 114 may further serve as a scaffold for new cell-growth, or a scaffold material may be used in conjunction with the tissue interface 114 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may comprise or consist of, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 116 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 116 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minn.; polyurethane (PU) drape, commercially available from Avery Dennison Corporation, Pasadena, Calif.; polyether block polyamide copolymer (PEBAX), for example, from Arkema S.A., Colombes, France; and Inspire 2301 and Inspire 2327 polyurethane films, commercially available from Expopack Advanced Coatings, Wrexham, United Kingdom. In some embodiments, the cover 116 may comprise INSPIRE 2301 having an MVTR (upright cup technique) of 2600 $g/m^2/24$ hours and a thickness of about 30 microns.

An attachment device may be used to attach the cover 116 to an attachment surface, such as undamaged epidermis, a gasket, or another cover. The attachment device may take many forms. For example, an attachment device may be a medically-acceptable, pressure-sensitive adhesive configured to bond the cover 116 to epidermis around a tissue site. In some embodiments, for example, some or all of the cover 116 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In operation, the tissue interface 114 may be placed within, over, on, or otherwise proximate to a tissue site. If the tissue site is a wound, for example, the tissue interface 114 may partially or completely fill the wound, or it may be placed over the wound. The cover 116 may be placed over the tissue interface 114 and sealed to an attachment surface near a tissue site. For example, the cover 116 may be sealed to undamaged epidermis peripheral to a tissue site. Thus, the dressing 104 can provide a sealed therapeutic environment proximate to a tissue site, substantially isolated from the external environment, and the negative-pressure source 102 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream"

implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 114 in the sealed therapeutic environment can induce macro-strain and micro-strain in the tissue site. Negative pressure can also remove exudate and other fluid from a tissue site, which can be collected in container 106.

In some embodiments, the controller 108 may receive and process data from one or more sensors, such as the first sensor 110. The controller 108 may also control the operation of one or more components of the therapy system 100 to manage the pressure delivered to the tissue interface 114. In some embodiments, controller 108 may include an input for receiving a desired target pressure and may be programmed for processing data relating to the setting and inputting of the target pressure to be applied to the tissue interface 114. In some example embodiments, the target pressure may be a fixed pressure value set by an operator as the target negative pressure desired for therapy at a tissue site and then provided as input to the controller 108. The target pressure may vary from tissue site to tissue site based on the type of tissue forming a tissue site, the type of injury or wound (if any), the medical condition of the patient, and the preference of the attending physician. After selecting a desired target pressure, the controller 108 can operate the negative-pressure source 102 in one or more control modes based on the target pressure and may receive feedback from one or more sensors to maintain the target pressure at the tissue interface 114.

Figure 2:
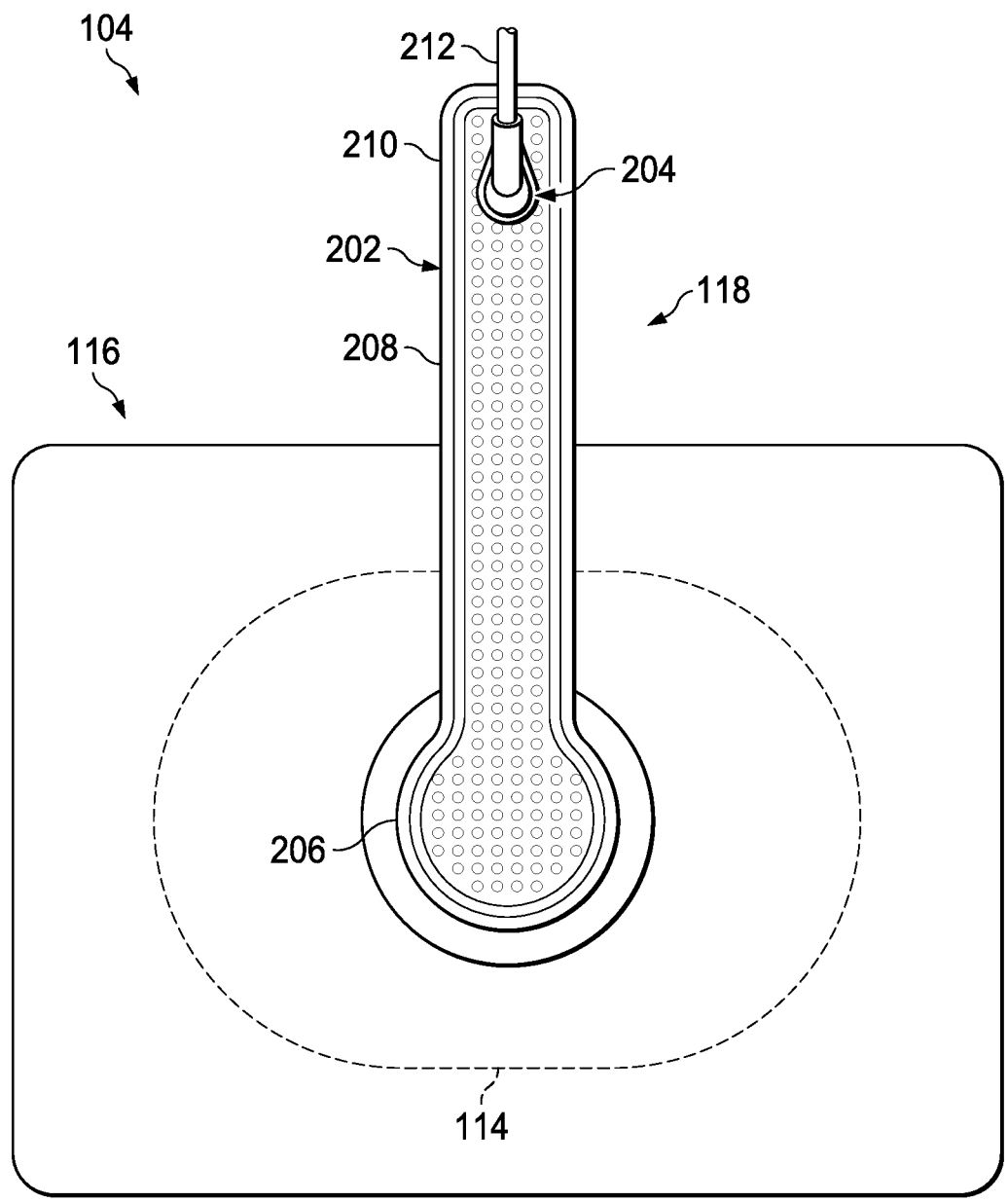
FIG. 2 is a plan view of a dressing, showing additional details that may be associated with some example embodiments of the therapy system of FIG. 1.

FIG. 2 is a plan view of an example of the dressing 104, showing additional details that may be associated with some embodiments. As illustrated, the dressing interface 118 may be sized and configured to be positioned at least partially on top of the tissue interface 114 and cover 116 of the dressing 104, and may be affixed or connected to a central portion of the cover 116. For example, the dressing interface 118 may be configured to be fluidly connected to the tissue interface 114 through an opening in the cover 116. The dressing interface 118 may be configured to fluidly connect the tissue interface 114 either directly or indirectly to the negative-pressure source 102, as well as possibly to other components of the therapy system 100, such as the controller 108 or the first sensor 110.

In some embodiments, the dressing interface 118 may include a bridge 202 and a connector 204. The bridge 202 may comprise a first end 206, a middle section 208, and a second end 210. The first end 206 may be adapted to be positioned in fluid communication with the tissue interface 114. For example, the first end 206 may be fluidly coupled to the tissue interface 114 through an aperture in the cover 116. The middle section 208 may be configured to fluidly couple the first end 206 to the second end 210. The second end 210 may be configured to fluidly couple the middle section 208 to the connector 204 or to another conduit, such as a conduit 212. The connector 204 may be configured for fluidly coupling the bridge 202 to the conduit 212, which may be coupled to the negative-pressure source 102.

Figure 3:
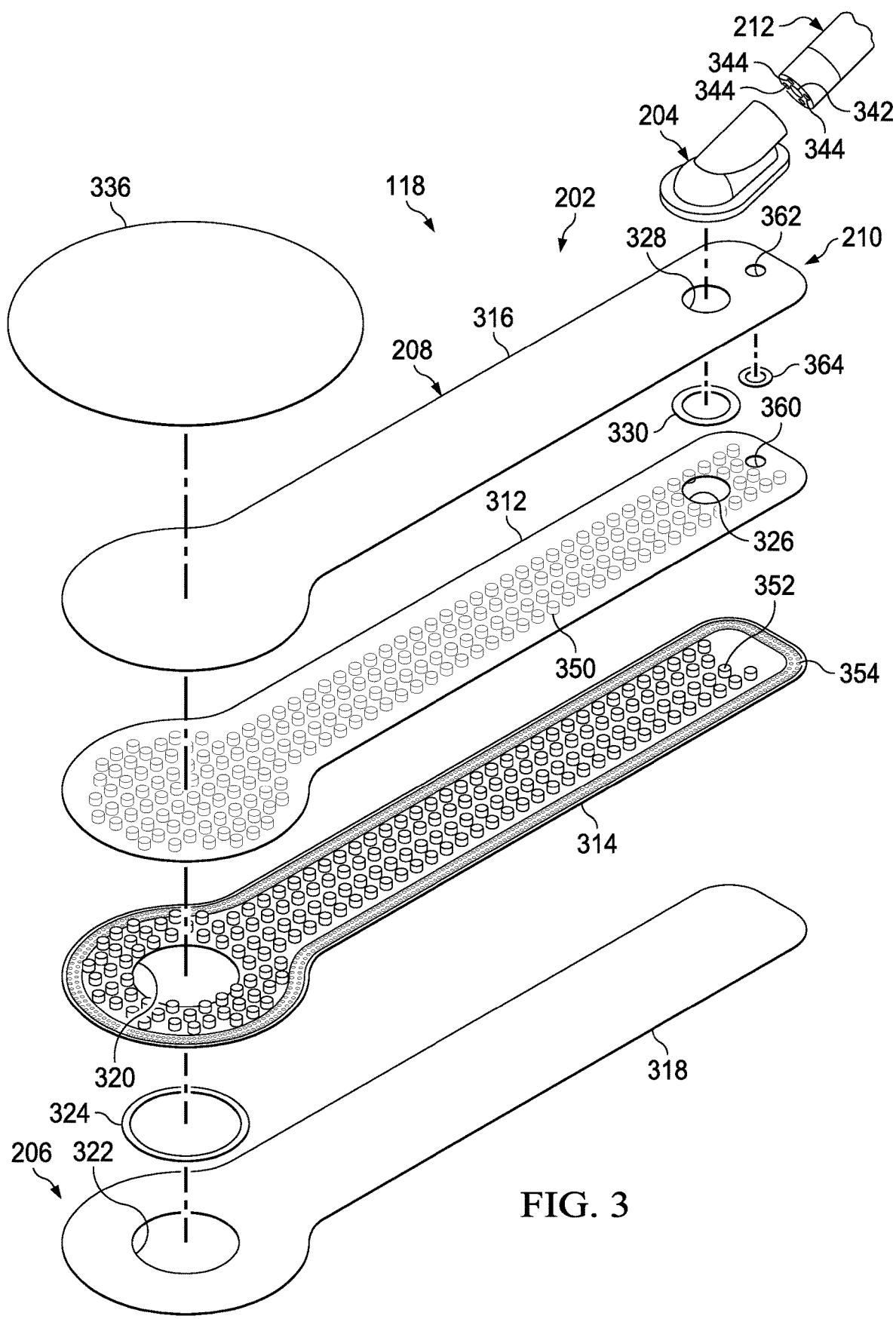
FIG. 3 is a perspective assembly view of a dressing interface having a low-profile structure that may be associated with some example embodiments of the dressing of FIG. 2 and therapy system of FIG. 1.

FIG. 3 is an assembly view of the dressing interface 118 of FIG. 2, according to some example embodiments. The bridge 202 may have a low profile structure that is substantially flat and flexible, but also compressible without occluding or blocking the one or more fluid pathways between the tissue interface 114 and the connector 204 for delivering negative pressure to the dressing 104. In some embodiments, the bridge 202 of the dressing interface 118 may comprise a top layer, such as a first layer 312, and a base layer, such as a second layer 314. The first layer 312 and the second layer 314 may both be formed from or include a polymeric film. The bridge 202 may further include a top encapsulation layer 316 and a base encapsulation layer 318, which may cover the first layer 312 and the second layer 314, respectively.

The first end 206 of the bridge 202 may comprise an opening to fluidly couple a sealed space of the bridge 202 to the tissue interface 114. More specifically, the second layer 314 may include a first aperture 320 at the first end 206 of the bridge 202. The base encapsulation layer 318 may also include an aperture, such as second aperture 322, which may be configured and positioned to align with the first aperture 320 of the second layer 314 of the bridge 202. The first end 206 of the bridge 202 may further comprise a first bond 324, which may be an adhesive ring or a weld, between the second layer 314 and the base encapsulation layer 318 to seal the first aperture 320 of the second layer 314 to the second aperture 322 of the base encapsulation layer 318 to prevent leakage of fluids flowing through the apertures.

The second end 210 of the bridge 202 may include an opening to fluidly couple a sealed space of the bridge 202 to the connector 204. More specifically, the first layer 312 may include a third aperture 326 at the second end 210 of the bridge 202. The top encapsulation layer 316 may also include an aperture, such as fourth aperture 328, which may be configured and positioned to align with the third aperture 326 of the first layer 312 of the bridge 202. The third aperture 326 of the first layer 312 and the fourth aperture 328 of the top encapsulation layer 316 may provide a port for fluidly coupling a sealed space of the bridge 202, such as a sealed space for communicating negative pressure, to the connector 204. The second end 210 of the bridge 202 may further include a second bond 330, which may be an adhesive ring or a weld, between the first layer 312 and the top encapsulation layer 316 to seal the third aperture 326 and the fourth aperture 328 to prevent leakage of fluids flowing through them to the connector 204. The second end 210 of the bridge 202 may also include a second opening to fluidly couple a second sealed space of the bridge 202 to the connector 204. For example, the first layer 312 may include a fifth aperture 360 at the second end 210 of the bridge 202. The top encapsulation layer 316 may also include an additional aperture, such as a sixth aperture 362, which may be configured and positioned to align with the fifth aperture 360 of the first layer 312. The fifth aperture 360 of the first layer 312 and the sixth aperture 362 of the top encapsulation layer 316 may provide an additional port for fluidly coupling a second sealed space of the bridge 202, such as a sealed space for transmitting pressure measurements, to the connector 204. A third bond 364 may also be placed between the first layer 312 and the top encapsulation layer 316 to seal the fifth aperture 360 and the sixth aperture 362. The connector 204 of the dressing interface 118 may have a structure comprising a semi-rigid elbow port.

In some embodiments, a top drape 336 may be utilized to cover the first end 206 of the bridge 202 to provide additional protection and support over the first end 206 of the bridge 202 when the bridge 202 is applied to a tissue site. In some embodiments, the top drape 336 may also be utilized to cover any adhesive that might be exposed from applying the cover 116, tissue interface 114, or bridge 202 to the tissue site. In some embodiments, the top drape 336 may be similar to the cover 116 described above and, as such, may be a polymer such as a polyurethane film.

In some embodiments, the dressing interface 118, including both the bridge 202 and the connector 204, may have a length that ranges between about 15 cm and about 30 cm. In some embodiments, the different sections and ends of the bridge 202 may be formed as a single device as shown. In other embodiments, the bridge 202 may include multiple separate components that may be coupled together to form the bridge 202.

In some embodiments, the first end 206 of the bridge 202 may be bulbous or any shape suitable for applying therapy to the tissue interface 114, and the shape may depend on the size and nature of the tissue site. Overall, the bridge 202 of the dressing interface 118 may be rather long and narrow in shape, and adapted to be fluidly coupled to conduit 212 through the connector 204 for delivering and also sensing negative pressure. In some embodiments, the conduit 212 may comprise a central lumen 342 for delivering negative pressure to the dressing interface 118 and one or more peripheral lumens 344 for sensing negative pressure in the dressing interface 118, other components of the dressing 104, and the tissue site. The other end of the conduit 212, and thus the other ends of the central lumen 342 and the one or more peripheral lumens 344 may be fluidly connected to the negative-pressure source 102 and a pressure sensor, such as the first sensor 110, respectively, either directly or indirectly through the container 106.

The bridge 202 of the dressing interface 118 may further include a plurality of features such as, for example, flexible projections, flexible standoffs, open cells, or closed cells, which may provide support to and facilitate open fluid communication through the one or more fluid pathways of the bridge 202. For example, the first layer 312 of the bridge 202 may include first closed cells 350 having a bottom portion extending from the first layer 312 and a top portion extending within a sealed space toward the second layer 314. Additionally, the second layer 314 of the bridge 202 may also include closed cells, such as second closed cells 352, having a bottom portion extending from the second layer 314 and a top portion extending within the sealed space toward the first layer 312. The first closed cells 350 and second closed cells 352 may provide a cushion within the sealed space between the first layer 312 and second layer 314 to help prevent the sealed space of the bridge 202 from collapsing as a result of external forces or due to delivery of negative pressure through the sealed space. Furthermore, in some embodiments, the bridge 202 may include auxiliary closed cells 354, which may be included as part of the second layer 314 and assist with defining one or more pressure-sensing pathways. For example, the auxiliary closed cells 354 may comprise a plurality of smaller closed cells arranged in a strip or border pattern around the perimeter of the second layer 314. The auxiliary closed cells 354 may be positioned and configured to facilitate open fluid communication within one or more sensing pathways, as described in further detail below. In some embodiments, the auxiliary closed cells 354 may additionally or alternatively be positioned around the border of the first layer 312. A range of sizes of closed cells may be employed, however in some embodiments, the first closed cells 350 and second closed cells 352 may have a diameter in a range of about 1 mm to about 10 mm, and the auxiliary closed cells 354 may have a diameter in a range of about 1 mm to about 3 mm. In some alternative embodiments, instead of closed cells, the bridge 202 may include projections or nodes having a flexibility similar to closed cells. In some further embodiments, the bridge 202 may not include projections, nodes, or closed cells, but instead may include a fabric material or foam between two or more of the layers of the bridge 202, to assist with supporting and maintaining open fluid pathways. In some example embodiments, the closed cells may be substantially airtight to inhibit collapsing of the closed cells from the application of negative pressure which could block the flow of fluid through the bridge 202. The closed cells may be substantially airtight when formed and have an internal pressure that is an ambient pressure. In another example embodiment, the closed cells may be inflated with air or other suitable gases such as, for example, carbon dioxide or nitrogen. The closed cells may be inflated to have an internal pressure greater than the atmospheric pressure to maintain their shape and resistance to collapsing under pressure and external forces. For example, the closed cells may be inflated to a pressure of up to about 25 psi above the atmospheric pressure so that they do not collapse. In yet additional embodiments, the bridge 202 may include other features or structures for facilitating fluid communication through the one or more fluid pathways, such as tubes that extend along the perimeter of the bridge 202 to provide pressure-sensing pathways.

Figure 4:
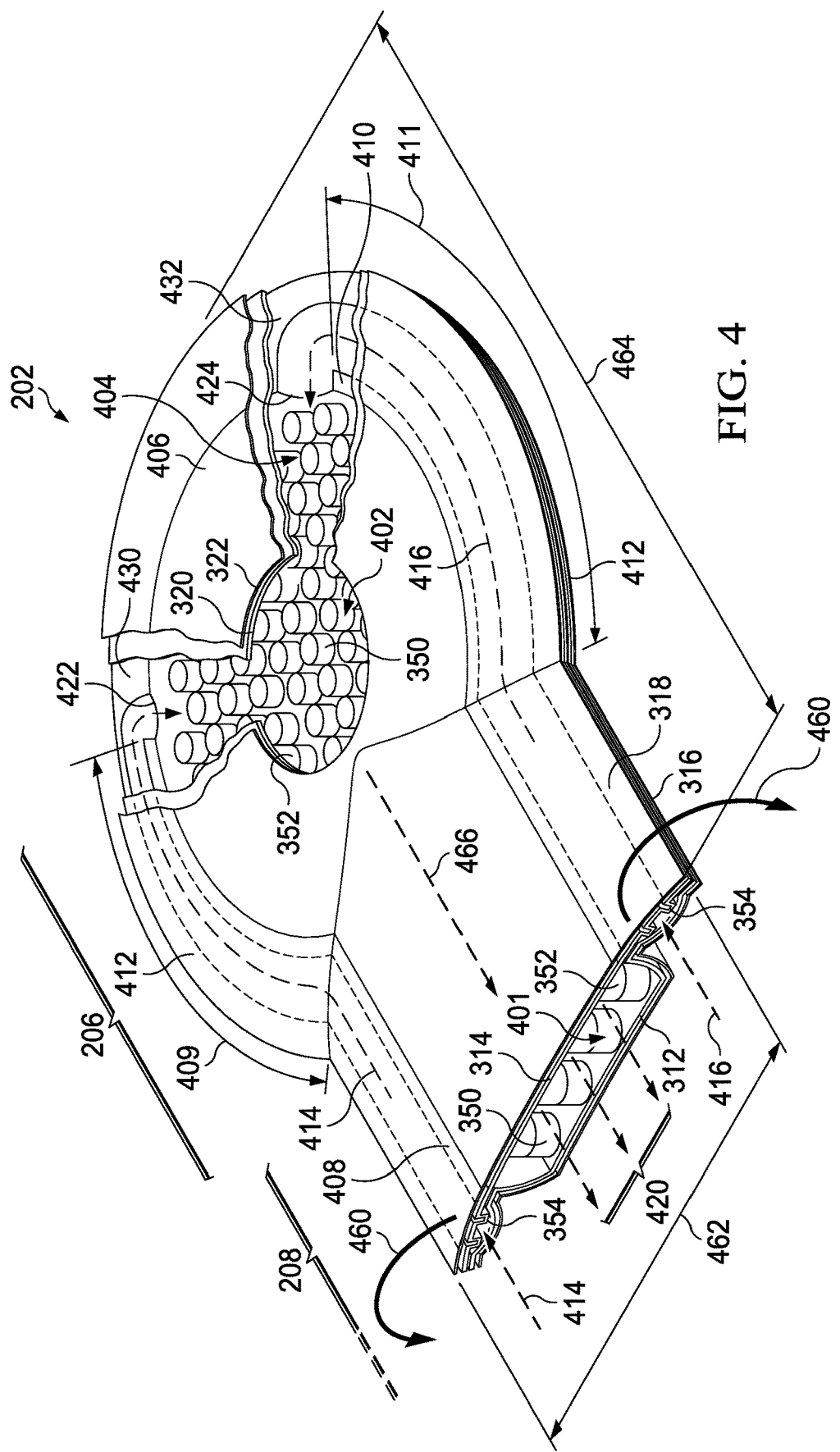
FIG. 4 is a segmented perspective bottom view of a portion of the dressing interface of FIG. 3, showing additional details that may be associated with some example embodiments.
Figure 5:
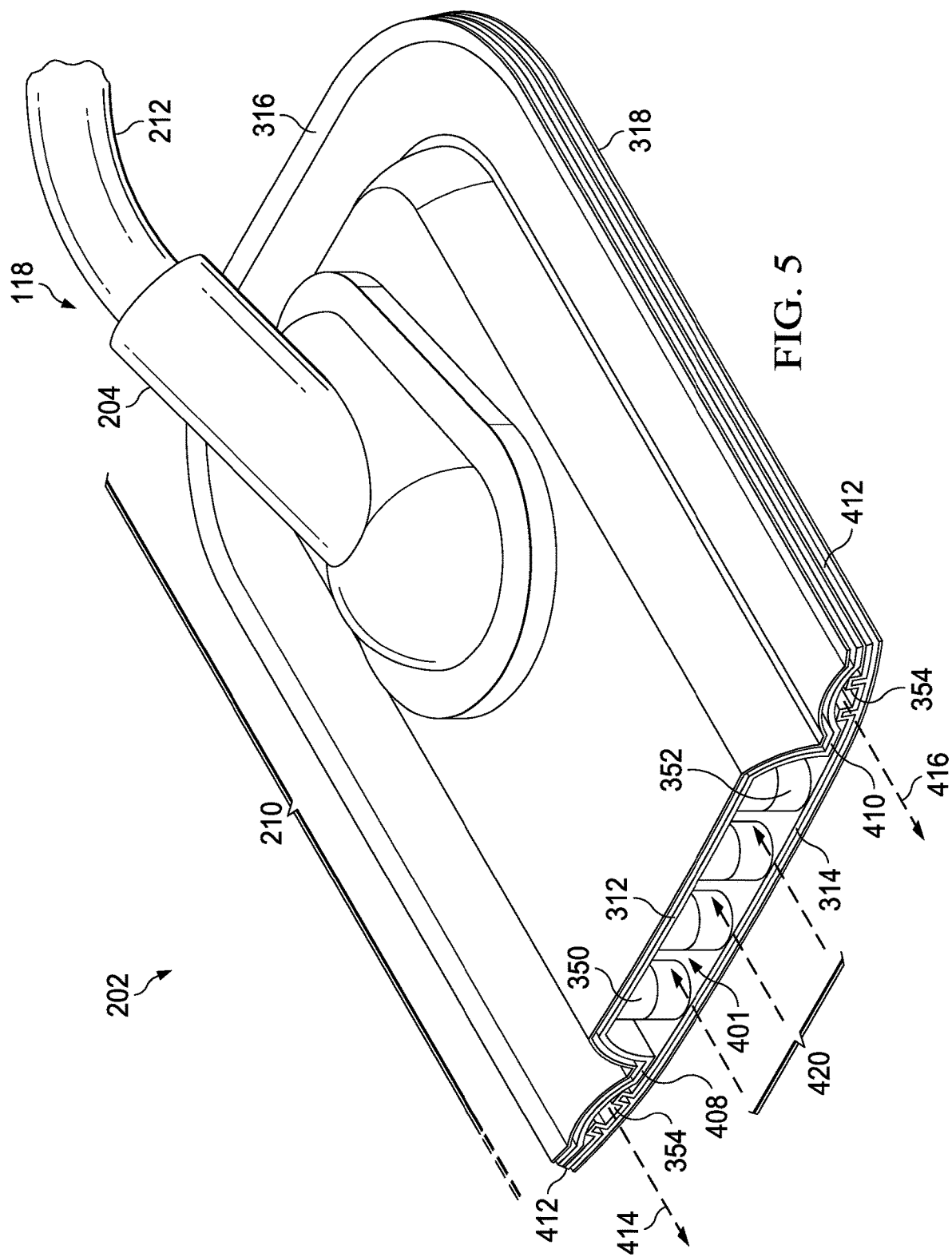
FIG. 5 is a segmented perspective top view of a portion of the dressing interface of FIG. 3, showing additional details that may be associated with some example embodiments.

FIGS. 4 and 5 illustrate additional details that may be associated with some examples of the bridge 202. For example, FIG. 4 is a segmented perspective bottom view of the first end 206 and a portion of the middle section 208 of the bridge 202 according to some illustrative embodiments. As shown in FIG. 4, the top encapsulation layer 316 may be coupled to a periphery of the base encapsulation layer 318. The top encapsulation layer 316, the base encapsulation layer 318, or both, may comprise a polymeric film in some embodiments. Between the top encapsulation layer 316 and the base encapsulation layer 318, the bridge 202 may further include the first layer 312 and the second layer 314 coupled to the first layer 312 around the periphery of the first layer 312 to form the sealed space 401 within the first end 206. The first layer 312 and the second layer 314 may be coupled to each other around the periphery of the bridge 202 to form the sealed space 401 by welding (RF or ultrasonic), heat sealing, or adhesive bonding such as, for example, using acrylics or cured adhesives. There are a variety of known methods for coupling the first layer 312 and the second layer 314 to form the sealed space 401 within the bridge 202. The top encapsulation layer 316 and the base encapsulation layer 318 may surround and form a seal around the first layer 312 and the second layer 314.

The first end 206 may further include an opening to fluidly couple the sealed space 401 of the bridge 202 to the tissue interface 114. The opening may be formed by the first aperture 320 in the second layer 314 and the second aperture 322 in the base encapsulation layer 318. The first aperture 320 in the second layer 314 and the second aperture 322 in the base encapsulation layer 318, along with the portion of the first layer 312 in the first end 206 may define a recessed space 402 within the sealed space 401 of the first end 206, wherein the recessed space 402 is adapted to be in fluid communication with the tissue interface 114 when the bridge 202 is disposed over the tissue site. The portion of the recessed space 402 that is covered by the second layer 314 and the base encapsulation layer 318 of the first end 206 may be referred to as a covered space 404.

In some embodiments, the first aperture 320 and the second aperture 322 may each have a diameter in a range between about 3.25 cm and about 17.5 cm. The size of the first aperture 320 and the second aperture 322 may be sufficiently large along with the recessed space 402 to obviate the need for precise alignment or sizing, as opposed to small holes requiring precise alignment with an opening in the cover 116. In some embodiments, the first aperture 320 and the second aperture 322 may even be larger than the opening in the cover 116. The first end 206 of the bridge 202 may also comprise an affixation surface 406, which may be used for coupling the first end 206 of the bridge 202 to the cover 116 and/or tissue interface 114. For example, the affixation surface 406 may comprise a bottom surface of the base encapsulation layer 318 at the first end 206 that may include an attachment device, such as an adhesive. Additionally, the affixation surface 406 may be covered by a release liner (not shown) to protect the adhesive prior to applying the bridge 202 to a tissue site. The remaining portions of the bottom surface of the base encapsulation layer 318 may also include an attachment device (not shown), such as an adhesive. For example, some embodiments of the bridge 202 may include one or more sections or patterns of an adhesive placed on an outer surface of the base encapsulation layer 318 for securing the bridge 202 to a patient's epidermis or another component of the dressing 104.

The bridge 202 may further comprise at least one wall or barrier coupled between the first layer 312 and the second layer 314. In some embodiments, a first barrier 408 may extend from the first end 206 of the bridge 202 through the middle section 208 to the second end 210 of the bridge 202 to form at least two fluid pathways between the first layer 312 and the second layer 314 within the sealed space 401 of the bridge 202. In some embodiments, the bridge 202 may further include a second barrier 410 coupled between the first layer 312 and the second layer 314 that may extend from the first end 206 to the second end 210 of the bridge 202 to form a third fluid pathway between the first layer 312 and the second layer 314 within the bridge 202. In some embodiments, the first barrier 408 and the second barrier 410 may comprise a polymeric film coupled between the first layer 312 and the second layer 314. In some additional embodiments, the first barrier 408 and the second barrier 410 may be formed from a weld (RF or ultrasonic), a heat seal, an adhesive bond, or a combination of any of the foregoing between the first layer 312 and the second layer 314.

In some embodiments, the first barrier 408, in conjunction with a flange 412 formed by the first layer 312 and the second layer 314 being coupled together around a perimeter of the bridge 202, may form a fluid conductor or pathway, such as first sensing pathway 414. For example, the first sensing pathway 414 may be formed in the sealed space 401 between the first layer 312 and the second layer 314 having the first barrier 408 and the flange 412 as borders. Similarly, a second sensing pathway 416 may be formed in the sealed space 401 between the first layer 312 and the second layer 314 having the second barrier 410 and the flange 412 as borders. Thus, in some embodiments, the bridge 202 may include three separate fluid pathways within the sealed space 401 between the first layer 312 and the second layer 314. In some embodiments, one of the fluid pathways may be utilized for delivering negative pressure from the conduit 212 through the connector 204 and the bridge 202 to the tissue interface 114, while two of the fluid pathways, such as the first sensing pathway 414 and the second sensing pathway 416, may be dedicated to sensing or measuring pressure. For example, the sealed space 401 of the bridge 202 between the first barrier 408 and the second barrier 410 may comprise a negative-pressure pathway 420 and may be adapted for delivering negative pressure to the first end 206 of the bridge 202. One or both of the first sensing pathway 414 and the second sensing pathway 416 may be for providing negative-pressure feedback measurements.

As shown in FIG. 4, the first sensing pathway 414 and the second sensing pathway 416 may terminate at a first opening 422 and second opening 424, respectively, at the covered space 404, and thus be in fluid communication with the recessed space 402. In some embodiments, the first sensing pathway 414 and the second sensing pathway 416 may have a height having a value in a range between about 0.25 mm and about 3 mm, and in some embodiments may have a height in a range between about 0.5 mm and about 1.5 mm. In some embodiments, the first sensing pathway 414 and the second sensing pathway 416 may have a width having a value in a range between about 1 mm and about 7.5 mm. Thus, in some example embodiments, the first sensing pathway 414 and the second sensing pathway 416 may have a cross-sectional area having a value in a range between about 0.17 mm$^2$ and about 16.77 mm$^2$. In some embodiments, the first sensing pathway 414 and the second sensing pathway 416 may have a cross-sectional area having a value in a range between about 0.1 mm$^2$ and about 18 mm$^2$. In some embodiments of the bridge 202, both of the sensing pathways, the first sensing pathway 414 and the second sensing pathway 416, are separate from, and side-by-side with, the negative-pressure pathway 420. The side-by-side orientation of the first sensing pathway 414 and the second sensing pathway 416 with the negative-pressure pathway 420 forms a bridge 202 that may be generally flatter than a conduit or similar fluid conductor, while still being resistant to collapsing under pressure that could otherwise block fluid flow through one or more of the pathways of the bridge 202.

In some example embodiments, each of the first barrier 408 and the second barrier 410 may each extend an angular distance 409, 411, respectively, around the first end 206 of the bridge 202 and cooperate with a first blocking wall 430 and a second blocking wall 432, respectively, to form extensions of the first sensing pathway 414 and the second sensing pathway 416, respectively, that may be fluidly coupled to the recessed space 402. The angular distance each of the first barrier 408 and the second barrier 410 extends around the first end 206 of the bridge 202 may vary, and thus the first opening 422 of the first sensing pathway 414 and the second opening 424 of the second sensing pathway 416 may each be positioned at different locations around the first end 206 of the bridge 202, depending on the particular embodiment. The sensing pathways, namely the first sensing pathway 414 and the second sensing pathway 416, may be in fluid communication with the recessed space 402 through the first opening 422 at an end of the first sensing pathway 414 and the second opening 424 at the end of the second sensing pathway 416, respectively. As such, the negative-pressure pathway 420 may be in fluid communication with the recessed space 402 and is adapted to deliver negative pressure to the tissue interface 114 through the recessed space 402, while the pressure-sensing pathways, the first sensing pathway 414 and the second sensing pathway 416, are adapted to sense the pressure within the recessed space 402 and within the sealed environment. The spacing of the first opening 422 and the second opening 424 from each other, and from the negative-pressure pathway 420, may allow the first sensing pathway 414 and second sensing pathway 416, to better avoid the flow of fluids, such as wound exudates, passing through the recessed space 402 from the tissue interface 114 to the negative-pressure pathway 420 when negative pressure is applied. Additionally, the first opening 422 and the second opening 424 may be sufficiently small for further restricting fluid flow into the first sensing pathway 414 and the second sensing pathway 416, respectively. For example, the first opening 422 and the second opening 424 may each have a cross-sectional area having a value in a range between about 0.17 mm$^2$ and about 16.77 mm$^2$. Additionally, in some embodiments, the first opening 422 and the second opening 424 may be arranged so that they each extend further into a center portion of the recessed space 402, which in some instances may warrant the omission of some of the closed cells 350 and 352 in the respective areas of the covered space 404.

As also shown in FIG. 4, the first layer 312 may comprise first closed cells 350, which may have a bottom portion extending from the first layer 312 and a top portion extending within the negative-pressure pathway 420 toward the second layer 314. Additionally, the second layer 314 may comprise second closed cells 352, which may have a bottom portion extending from the second layer 314 and a top portion extending within the negative-pressure pathway 420 toward the first layer 312. In some embodiments the top portion of the first closed cells 350 may come in contact with the second layer 314, and in some additional embodiments, the top portion of the first closed cells 350 may be coupled to the second layer 314. In some embodiments, top portions of the first closed cells 350 and the second closed cells 352 may be aligned so as to abut each other, while additionally or alternatively, some embodiments may include first closed cells 350 and second closed cells 352 that may be positioned or fit between each other when the first layer 312 and the second layer 314 are positioned adjacent to each other.

In some embodiments, the top portion of the first closed cells 350 may extend from the first layer 312 within the recessed space 402 and toward the first aperture 320 and the second aperture 322 in the first end 206 of the bridge 202. For example, the first closed cells 350 may extend from the first layer 312 through the first aperture 320 of the second layer 314 and the second aperture 322 of the base encapsulation layer 318 and may be adapted to come in direct contact with the tissue interface 114 when the bridge 202 is positioned adjacent the tissue interface 114. Therefore, at least in some embodiments, due to the first aperture 320 in the second layer 314, the second layer 314 will not include any projections or closed cells within the recessed space 402. However, in the sealed space 401 outside of the recessed space 402, the second layer 314 may also include second closed cells 352 having bottom portions extending from the second layer 314 and top portions extending within the sealed space 401 toward the first layer 312.

Depending on the particular embodiment, the closed cells, such as the first closed cells 350 and the second closed cells 352 may be formed from a non-porous, polymeric film that may comprise any flexible material that can be manipulated to enclose closed cells, including various thermoplastic materials, e.g., polyethylene homopolymer or copolymer, polypropylene homopolymer or copolymer, etc. Non-limiting examples of suitable thermoplastic polymers include polyethylene homopolymers, such as low density polyethylene (LDPE) and high density polyethylene (HDPE), and polyethylene copolymers such as, e.g., ionomers, EVA, EMA, heterogeneous (Zeigler-Natta catalyzed) ethylene/alpha-olefin copolymers, and homogeneous (metallocene, single-cite catalyzed) ethylene/alpha-olefin copolymers. Ethylene/alpha-olefin copolymers are copolymers of ethylene with one or more comonomers selected from $C_3$ to $C_{20}$ alpha-olefins, such as 1-butene, 1-pentene, 1-hexene, 1-octene, methyl pentene and the like, in which the polymer molecules comprise long chains with relatively few side chain branches, including linear low density polyethylene (LLDPE), linear medium density polyethylene (LMDPE), very low density polyethylene (VLDPE), and ultra-low density polyethylene (ULDPE). Various other materials are also suitable such as, e.g., polypropylene homopolymer or polypropylene copolymer (e.g., propylene/ethylene copolymer), polyesters, polystyrenes, polyamides, polycarbonates, etc.

In some example embodiments, the first layer 312 and the second layer 314, including the first closed cells 350 and the second closed cells 352, respectively, may comprise a polymeric film such as, for example, a thermoplastic polyurethane (TPU) film that is permeable to water vapor but impermeable to liquid. The first layer 312 and the second layer 314 may comprise various degrees of breathability and may have MVTRs that are proportional to their thickness. For example, the MVTR may be at least 300 grams per square meter per twenty-four hours in some embodiments. For permeable materials, the permeability generally should be low enough to maintain a desired negative pressure for the desired negative pressure treatment. In some embodiments, the first layer 312 and/or the second layer 314 may each be formed from two sheets of polymeric film having inner surfaces coupled together to form sealed regions defining the plurality of closed cells, such as the first closed cells 350 and the second closed cells 352. The two sheets of polymeric film may be a single sheet of material having two laminae or two separate sheets that are coupled together to form the closed cells. The sheets of polymeric film may initially be separate sheets that are brought into superposition and sealed or they may be formed by folding a single sheet unto itself with a heat sealable surface facing inward. Each sheet of the polymeric film also may be a monolayer or multilayer structure depending on the application or the desired structure of the closed cells.

The closed cells formed by the polymeric film may be structured so that they do not completely collapse from apposition forces resulting from the application of negative pressure and/or external forces to the bridge 202 and the tissue site when the bridge 202 is positioned at the tissue site and negative pressure is applied to the bridge 202. In one embodiment, the polymeric film possesses sufficient tensile strength to resist stretching under the apposition forces created by negative-pressure wound therapy. The tensile strength of a material is the ability of material to resist stretching as represented by a stress-strain curve, where stress is the force per unit area, i.e., pascals (Pa), newtons per square meter (N/m$^2$), or pounds per square inch (psi). The ultimate tensile strength (UTS) is the maximum stress the material can withstand while being stretched before failing or breaking. Many materials display a linear elastic behavior defined by a linear stress-strain relationship often extending up to a nonlinear region represented by the yield point, i.e., the yield strength of a material. For example, high-density polyethylene (HDPE) has a high tensile strength, and low-density polyethylene (LDPE) has a slightly lower tensile strength, and both may be suitable materials for the sheets of non-porous, polymeric film as set forth above. Linear low density polyethylene (LLDPE) is often used as well because the material stretches very little as the force is increased up to the yield point of the material. Thus, the closed cells are able to resist collapsing (or stretching) when subjected to an external force or pressure. For example, HDPE has a UTS of about 37 MPa and may have a yield strength that ranges from about 26 to about 33 MPa depending on the thickness of the material, while LDPE has somewhat lower values.

In some example embodiments, the first layer 312 and the second layer 314, including the first closed cells 350 and the second closed cells 352, respectively, may comprise a thermoplastic polyurethane (TPU) film, as described above. The thermoplastic polyurethane film may be, for example, a Platilon® thermoplastic polyurethane film available from Convestro LLC, which may have a UTS of about 60 MPa and may have a yield strength of approximately 11 MPa or greater than about 10 MPa, depending on the thickness of the material. Therefore, in some example embodiments, it is desirable that the non-porous, polymeric film may have a yield strength greater than about 10 MPa depending on the type and thickness of material. A material having a lower yield strength may be too stretchable and, therefore, more susceptible to breaking with the application of small amounts of compression and/or apposition forces. In some embodiments, the first layer 312 and/or the second layer 314 may be formed of two sheets that may each comprise a polyurethane film having a thickness within a range of about 200 microns to about 600 microns. In some example embodiments, each of the two sheets may have a thickness of about 250 microns. In some other embodiments, each of the two sheets may have a thickness of about 500 microns. After the closed cells have been fabricated, the walls of the closed cells may have a thickness relative to the thickness of the individual sheets, as defined by a draw ratio, i.e., the ratio of the average height of the closed cells to the average thickness of each of the two sheets. In some example embodiments, the closed cells may have a generally tubular shape. In some example embodiments, each of the two sheets may have an average thickness of about 500 microns, and the closed cells may have an average height in a range between about 2.0 mm and 5.0 mm. Consequently, the closed cells have a draw ratio ranging from about 4:1 to about 10:1 for heights of 2.0 mm and 5.0 mm, respectively. In some embodiments, closed cells that are generally hemispherical or tubular in shape may have a diameter between about 1.0 mm and about 10.0 mm. In some other embodiments, the closed cells may have a diameter between about 2.0 mm and about 5.0 mm. In some embodiments, the closed cells may also have a pitch, i.e., the center-to-center distance between each of the closed cells, between about 1 mm and about 10 mm. In some other embodiments, the closed cells may also have a pitch between about 2 mm and about 3 mm. The two sheets may each have the same or different thickness and/or flexibility, but may be substantially non-stretchable so that the closed cells may maintain a generally constant volume without bursting after a compression force or negative pressure is applied to the bridge 202. Consequently, even when a load is applied to the bridge 202 which squeezes the closed cells into a different shape, the closed cells may be sufficiently flexible to recover their original shape after being squeezed, without bursting.

As also illustrated in FIG. 4, at least a portion or section of the bridge 202 may comprise a curved shape, such as the curve indicated by arrows 460. The curve of the bridge 202 may extend across the width 462 of the bridge 202, and may span along a substantial portion of the length 464 of the bridge 202. For example, in some embodiments the middle section 208 of the bridge 202 may be curved. In alternative embodiments, at least a portion of the first end 206 and/or second end 210 of the bridge 202 may also be curved. To accomplish the curvature of the bridge 202, the one or more layers included in at least the curved portions of the bridge 202, such as the first layer 312, the second layer 314, the top encapsulation layer 316, and the base encapsulation layer 318 may be assembled in a substantially flat stack, and then treated or further manufactured, such as by being welded together, which may increase the curvature at edges of the bridge 202. For example, the one or more layers included in the bridge 202 may be arranged in a stacked formation and permanently bonded together using RF/HF welding. Additionally or alternatively, the curvature of the bridge 202 may be achieved by providing one or more of the layers of the bridge 202 in a pre-curved configuration.

As shown in FIG. 4, the base encapsulation layer 318 may provide a smooth surface having a substantially flat portion and curved portions at the outer regions of the width 462 of the bridge 202. As also shown in FIG. 4, the negative-pressure pathway 420 and the first sensing pathway 414 and the second sensing pathway 416 may protrude from the opposite surface of the bridge 202 formed by the top encapsulation layer 316. Generally, the curvature of the base encapsulation layer 318 may be greater in the regions of the bridge 202 outboard of the negative-pressure pathway 420. In some embodiments, the base encapsulation layer 318 may be substantially flat between the first barrier 408 and the second barrier 410, and the curvature of the base encapsulation layer 318 may increase between the first barrier 408 and the respective adjacent edge of the flange 412 and between the second barrier 410 and the respective adjacent edge of the flange 412. In some embodiments, the curvature of the bridge 202 may be primarily, or in some instances solely, increased within outer portions of the bridge 202.

More specifically, in some embodiments, the starting points of curvature, or hinge lines, may be along weld lines formed at either or both of the innermost edge of the first barrier 408 and/or the innermost edge of the second barrier 410. Accordingly, the first sensing pathway 414 and the second sensing pathway 416 may be in the portions of the bridge 202 that are bent or curved upwards. In some alternative embodiments, the hinge line may be coincident with a centerline 466 of the bridge 202.

In some embodiments, the degree of curvature of the bridge 202 may be tailored or controlled in production by increasing the width of the welds forming either or both of the first barrier 408 and the second barrier 410. The degree of curvature of the bridge 202 may also be adjusted by increasing the offset of the welds forming either or both of the first barrier 408 and the second barrier 410 from the perimeter edges of the bridge 202, such as the perimeter edges of the middle section 208 of the bridge 202. Furthermore, the degree of curvature may be increased when the bridge 202 is subjected to an internal negative pressure, such as negative pressure transmitted through the negative-pressure pathway 420, as required during routine usage of the bridge 202 and dressing interface 118. For example, the typical magnitude of the internal negative pressure, often between −25 mmHg and −200 mmHg, may cause the bridge 202 to curve or bring the outer portions of the bridge 202 containing the first sensing pathway 414 and the second sensing pathway 416 away from the skin of a patient. By bringing the outer portions of the bridge 202 containing the first sensing pathway 414 and second sensing pathway 416 away from contact with a patient's skin, the risk of build-up of localized pressure points throughout the pressure-sensing pathways, which may otherwise interfere with pressure-sensing measurements, may be mitigated or avoided. Additionally, since in some embodiments the pressure-sensing pathways may comprise somewhat rigid conduits, tubes, or projections, reducing contact between the outer portions of the bridge 202 and the patient may reduce points of discomfort.

Some embodiments of the bridge 202 may further include one or more additional means for adhering portions of the bridge 202 to a patient, so as to ensure proper curvature of the appropriate portions of the bridge 202. For example, portions of the outer surface of the base encapsulation layer 318 in the middle section 208 of the bridge 202 may be coated with a low-tack material, such as a hydrogel, silicone gel, polyurethane gel, or a hydrocolloid material. One or more areas of coating may be located along and/or adjacent to a centerline 466 of the bridge 202, which may ensure that the softest, most conformable area of the middle section 208 of the bridge 202 remains in contact with the patient and providing confidence to the caregiver that the risk of localized pressure build-ups associated with the one or more pressure-sensing pathways has been mitigated. Including the means for adherence along or adjacent to the centerline 466 of the bridge 202 may also assist with maintaining the correct position of the bridge 202 and dressing interface 118 during therapy, providing additional confidence to both patients and caregivers that efficient therapy may be administered.

FIG. 5 is a segmented perspective top view of the second end 210 of the bridge 202 according to some illustrative embodiments. As shown in FIG. 5, the second end 210 of the bridge 202 may include a top encapsulation layer 316 and a base encapsulation layer 318 coupled to the top encapsulation layer 316 around the periphery of the top encapsulation layer 316. The first layer 312 and the second layer 314 may be positioned between the top encapsulation layer 316 and the base encapsulation layer 318. The second layer 314 may be coupled to the first layer 312 around the periphery of the first layer 312 to form the sealed space 401 within the second end 210 of the bridge 202.

In some example embodiments, the negative-pressure pathway 420, the first sensing pathway 414, and the second sensing pathway 416 may be fluidly coupled to the conduit 212 by the connector 204 at the second end 210 of the bridge 202. For example, the negative-pressure pathway 420 may be fluidly coupled to the central lumen 342 of the conduit 212 so that the negative-pressure pathway 420 may function to deliver negative pressure to the tissue interface 114. The first sensing pathway 414 and the second sensing pathway 416 may be fluidly coupled to the peripheral lumens 344 so that the first sensing pathway 414 and the second sensing pathway 416 may function to sense negative pressure at the tissue interface 114. Each of the first sensing pathway 414 and the second sensing pathway 416 may be fluidly coupled directly to one of the peripheral lumens 344. In some additional or alternative embodiments, both of the first sensing pathway 414 and the second sensing pathway 416 may be fluidly coupled to a single space within the connector 204 that is also fluidly coupled to the peripheral lumens 344. In some embodiments, the other ends of the first sensing pathway 414 and the second sensing pathway 416 may terminate in a common space within the first end 206 of the bridge 202.

Figure 6:
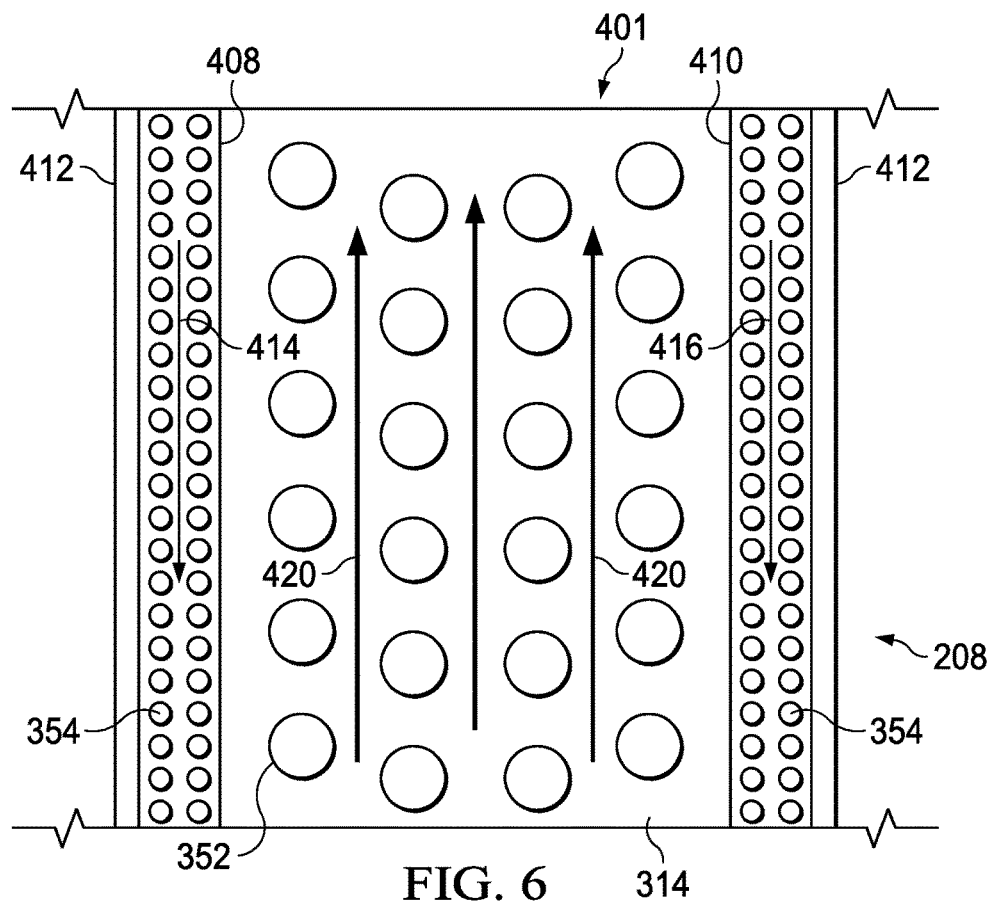
FIG. 6 is a plan view of a portion of the bridge of the dressing interface of FIGS. 4-5, showing some additional features that may be associated with some embodiments.

FIG. 6 is a plan view of a middle section 208 of the bridge 202 showing some additional details according to some example embodiments. As shown in FIG. 6, the negative-pressure pathway 420 may include second closed cells 352 extending from the second layer 314, which may have a generally cylindrical shape. Although not shown in FIG. 6, in some embodiments, the first layer 312 of the bridge of FIGS. 4-5 may be substantially the same as the second layer 314. In some embodiments, each of the first layer 312 and/or the second layer 314 may comprise two sheets of polymeric film. A portion of each of the two sheets may have inner surfaces coupled to each other to form a sealed region that defines a plurality of closed cells. The closed cells and the sealed region may be formed from a process such as, for example, vacuum forming. In some embodiments, the sealed region may be formed by a heat seal between the inner surfaces of the two sheets, while the closed cells may be formed simultaneously by vacuum forming. In another example embodiment, the sealed region may be formed by adhesion between the two sheets. Alternatively, the two sheets may be adhesively bonded to each other. The sealed region may be flexible enough so that the bridge 202 is sufficiently flexible to be curved as well as to conform to the shape of a tissue site. The sealed region may define the base or the cross-sectional shape of the closed cells as being generally circular, as shown, but in other embodiments may define the base as being a rectangular or triangular shape, hexagonal shape, or other geometric or irregular shape. The closed cells may be formed with a volumetric shape corresponding to the cross-sectional shape of the closed cells. For example, the volumetric shape may be generally hemispherical in shape. In other example embodiments, the closed cells may be formed with a volumetric shape that is generally conical, cylindrical, tubular having a flattened or hemispherical end, or geodesic in shape.

In some embodiments, a portion of the closed cells may be textured with surface features, which may be protrusions or indentations to enhance the distribution of negative pressure and fluid flow through the bridge 202 to the tissue interface 114 and the tissue site. For example, at least some of the closed cells may be embossed with projections, or nodes. The nodes may be positioned on the top of some of the closed cells, and in particular, the nodes may be included on the closed cells of the first layer 312 that will extend into the recessed space 402 and may be placed in contact with the tissue interface 114 to enhance fluid flow to the tissue site. The nodes may be projections that are flexible or rigid, and may have different shapes, for example the shape of a spike, cone, pyramid, dome, cylinder, or rectangle.

In some additional embodiments, conduits such as chambers may be formed between closed cells and may fluidly connect the closed cells. The chambers may help better distribute the apposition force applied to the bridge 202 and closed cells as a result of the application of negative pressure because the volume of the chambers in combination with the closed cells is greater than the volume of the closed cells alone.

As also depicted in FIG. 6, the middle section 208 of the bridge 202 may include two pressure-sensing pathways, such as the first sensing pathway 414 and the second sensing pathway 416, which may span the length of the middle section 208 of the bridge 202 alongside and parallel to the negative-pressure pathway 420. The first sensing pathway 414 may be formed between the flange 412 of the bridge 202 and the first barrier 408, which may fluidly separate the first sensing pathway 414 from the negative-pressure pathway 420. Similarly, the second sensing pathway 416 may be formed between the flange 412 and the second barrier 410, which may fluidly separate the second sensing pathway 416 from the negative-pressure pathway 420. As also shown in FIG. 6, each of the first sensing pathway 414 and the second sensing pathway 416 may also include projections or closed cells, such as auxiliary closed cells 354.

Figure 7:
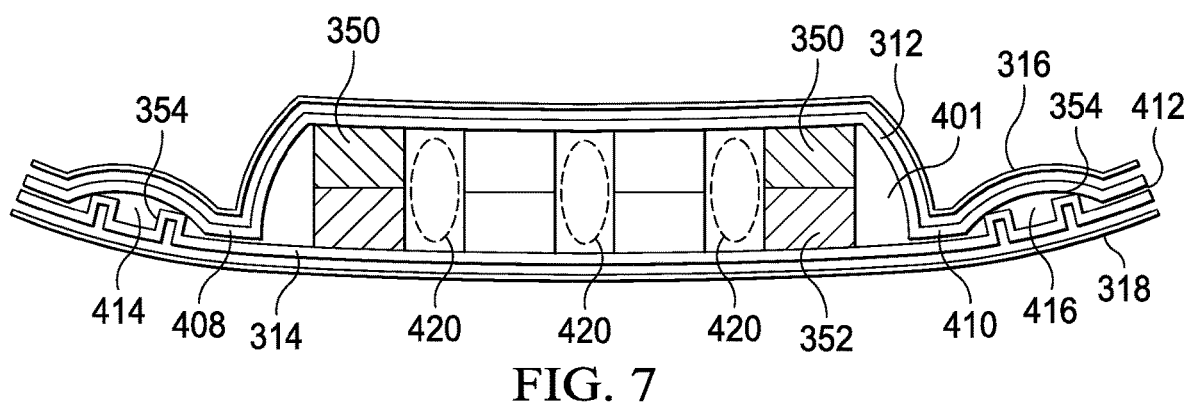
FIG. 7 is a section view of a portion of the bridge of the dressing interface of FIGS. 4-5, showing some additional features that may be associated with some example embodiments.

FIG. 7 is a section view of a portion of the middle section 208 of the bridge 202, showing some additional features according to some illustrative embodiments. As shown in FIG. 7, the negative-pressure pathway 420 may include first closed cells 350 extending from the first layer 312 and second closed cells 352 extending from the second layer 314. In some instances, each of the sets of closed cells may have closed cells having a generally cylindrical shape. As depicted in FIG. 7, in some embodiments, the two sets of closed cells, first closed cells 350 and second closed cells 352, may be opposingly aligned so that the upper portion of the first closed cells 350 extending from the first layer 312 face, or are aligned with, the upper portion of the second closed cells 352 extending from the second layer 314. Referring also to FIG. 6, in some embodiments, the middle section 208 of the bridge 202 may include four rows of each of the first closed cells 350 and second closed cells 352, wherein the closed cells of each of the first closed cells 350 and second closed cells 352 of the outer two rows are offset or staggered from the closed cells forming the two inside rows. In some alternative embodiments, the middle section 208 may include four rows of each of the first closed cells 350 and second closed cells 352 that are aligned both horizontally and vertically, rather than being offset or staggered with respect to each other. As also shown in FIG. 7, each of the first sensing pathway 414 and the second sensing pathway 416 may include auxiliary closed cells 354 to provide structure and maintain the form of the pressure-sensing pathways. In some alternative embodiments, one or both of the first sensing pathway 414 and the second sensing pathway 416 may comprise or be formed from tubes extending substantially along the length of the bridge 202.

As depicted in FIGS. 6 and 7, the first closed cells 350 and second closed cells 352 of the negative-pressure pathway 420 may have a larger diameter and pitch than the smaller auxiliary closed cells 354, which may assist with providing a flow of negative pressure to the tissue interface 114 to facilitate the removal of fluids and exudates. The auxiliary closed cells 354 disposed in the first sensing pathway 414 and the second sensing pathway 416 may have a noticeably smaller diameter and pitch, which may restrict fluid flow to facilitate pressure sensing within the recessed space 402 of the first end 206 of the bridge 202 while impeding the inflow of fluids and exudates into the first sensing pathway 414 and the second sensing pathway 416. The arrangement and dimensions of closed cells within both the negative-pressure pathway 420 and the one or more pressure-sensing pathways may be tailored to manage the delivery of negative pressure to the tissue interface 114 and the measuring of pressure within the sealed space 401 and the recessed space 402 of the bridge 202. For example, as visible in some of the previously-discussed figures, the first end 206 and the second end 210 of the bridge 202 may include closed cells having different shapes arranged in different patterns, which may be selected based on the particular tissue site and pneumatic requirements of negative-pressure delivery and pressure sensing. For example, the first end 206 of the bridge 202 may include closed cells that are arranged in a generally circular pattern within the recessed space 402, rather than the arrangement of rows of closed cells in middle section 208 of the bridge 202. Closed cells in the covered space 404 of the first end 206 surrounding the recessed space 402 may also have different shapes arranged in a different pattern.

Figure 8:
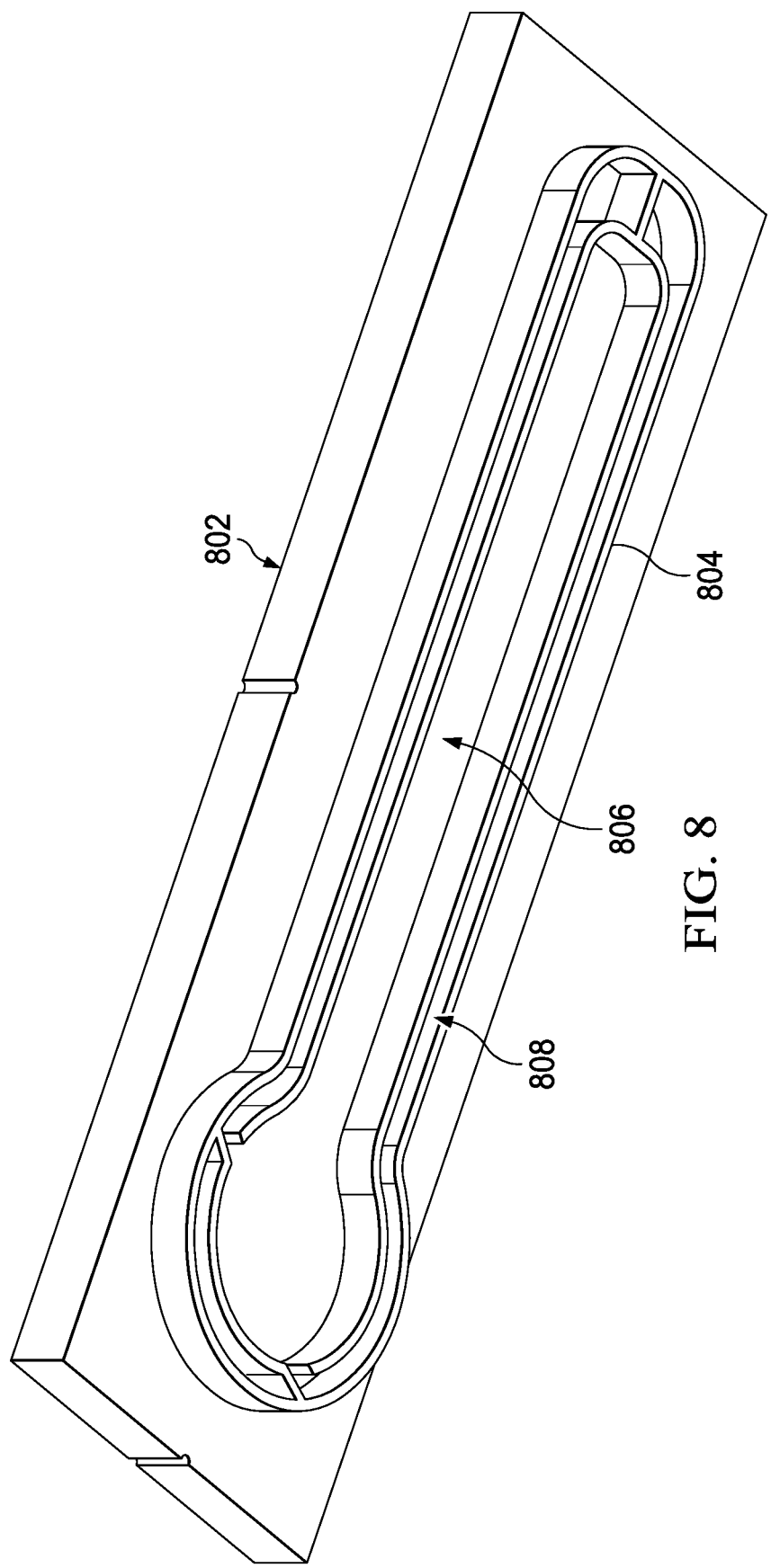
FIG. 8 is a schematic, perspective view of a welding apparatus useful for the assembly of a bridge of FIGS. 3-7, according to some example embodiments.

FIG. 8 is a schematic perspective view of a tool for use in welding together the multiple layers of a bridge, such as the bridge 202, according to some illustrative embodiments. For example, welding tool 802 may be used for creating the weld lines of the bridge 202, which may separate the multiple fluid pathways of the bridge 202. In some embodiments, the welding tool 802 may include a plurality of rails 804, which may be aligned and placed in contact with the portions of the layers of the bridge 202 that are to be welded together. For example, the rails 804 may be dimensioned to form one or more of the barrier regions separating a negative-pressure pathway of the bridge 202 from pressure-sensing pathways of the bridge 202, as well as to form the portions of the flange regions of the bridge 202 that are to be welded together. The welding tool 802 may also include a central cavity 806 and one or more peripheral cavities 808 positioned between the welding surfaces of the plurality of rails 804. In some embodiments, the central cavity 806 may provide a space to accommodate a negative-pressure pathway of the bridge 202 during the welding process, while the peripheral cavities 808 may accommodate the one or more pressure-sensing pathways.

Figure 9:
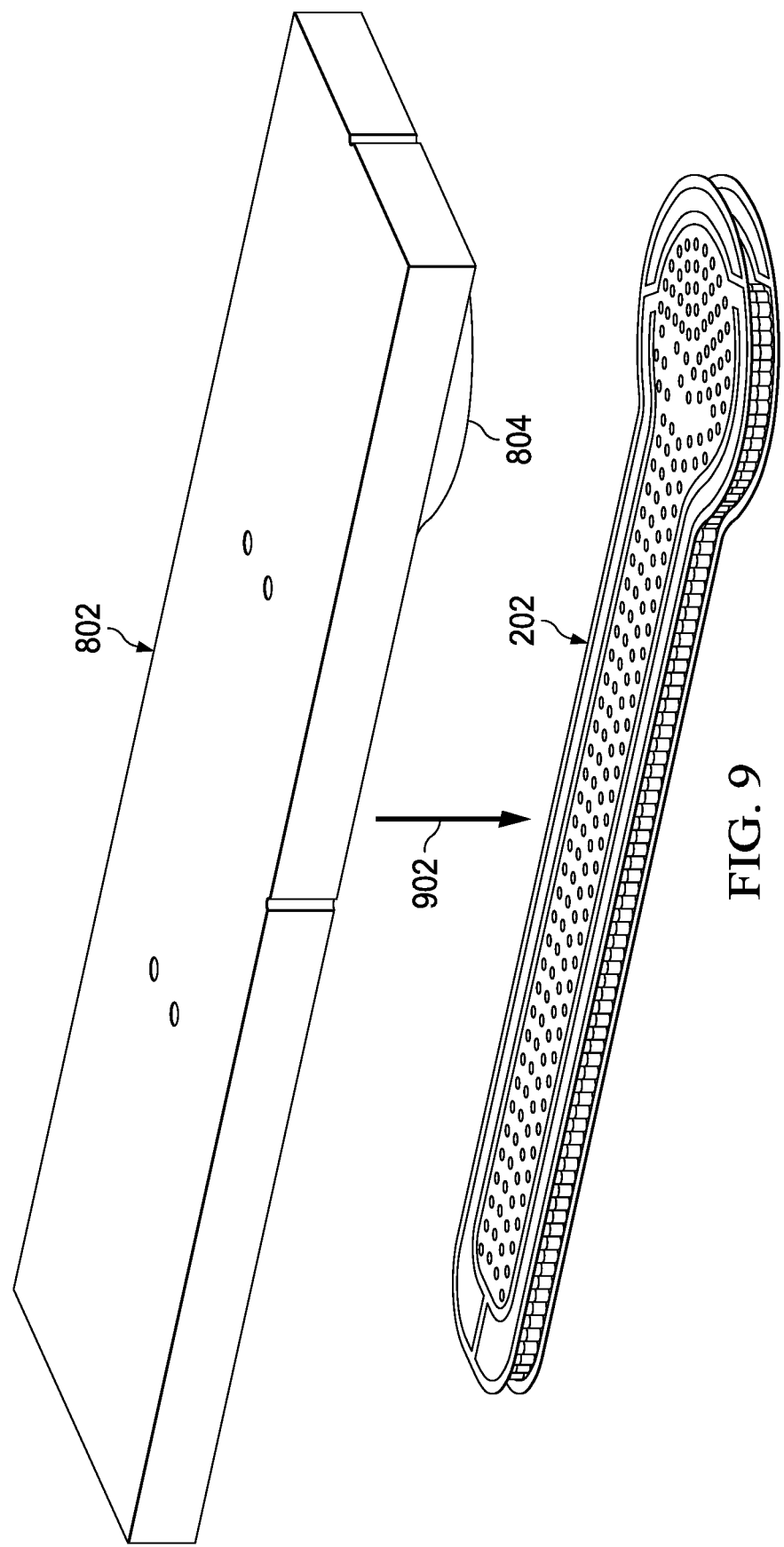
FIG. 9 is a schematic, perspective view showing some additional aspects of the welding apparatus of FIG. 8, according to some embodiments.

As illustrated by FIG. 9, in use, the welding tool 802 may be mounted in a RF/HF welder, and the welding tool 802 may be aligned with the assembled layers of the bridge 202 so that the plurality of rails 804 are aligned with the portions of the bridge 202 to be welded together between the portions of the bridge 202 that include the fluid pathways. The welding tool 802 may then be pressed downwards according to arrow 902 onto the bridge 202 in order to complete the welding of the appropriate portions of the multiple layers of the bridge 202.

Figure 10:
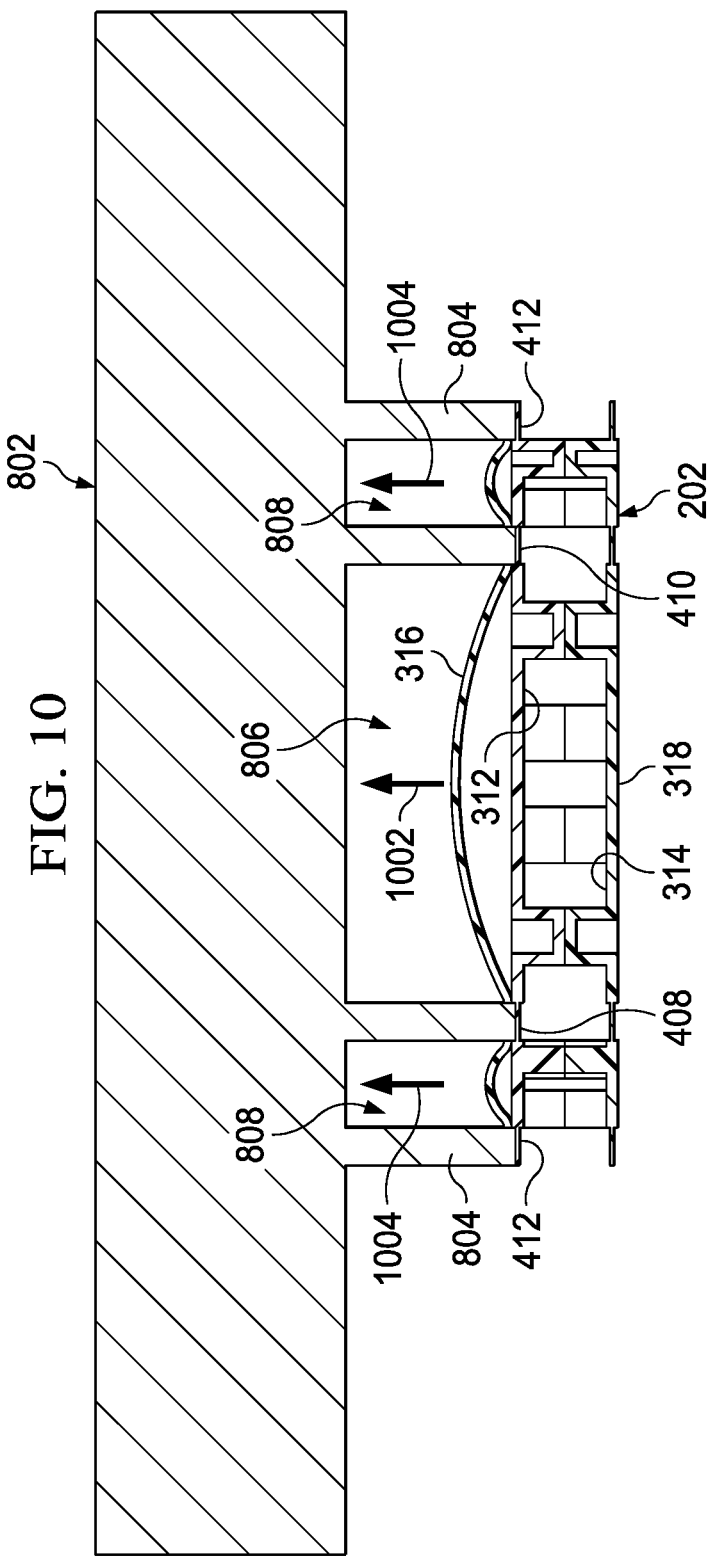
FIG. 10 is a schematic diagram showing some additional details associated with using the welding apparatus of FIG. 8 for the assembly of a bridge of FIGS. 3-7, according to some example embodiments.

Referring now also to FIG. 10, it can be seen how the process used for welding the layers of the bridge 202 may form the curved shape of the bridge 202. During the welding process, the plurality of rails 804 of the welding tool 802 may align with the regions of the bridge forming the first barrier 408, the second barrier 410, and the flange 412. The welding tool 802 may compress or squash the layers of the bridge 202 corresponding to the regions of the bridge 202 forming the first barrier 408, the second barrier 410, and the flange 412 onto a flat surface, such as a welding table or bench. The layers of the bridge 202 in closest proximity to the rails of the welding tool 802, such as the top encapsulation layer 316 and first layer 312, may be exposed to the highest amounts of heat and may be made to be thinner and weaker than the opposite layers of the bridge 202, such as the second layer 314 and the base encapsulation layer 318. The central cavity 806 and the peripheral cavities 808 may allow the material of the upper surface of the bridge 202 to expand upwards, according to arrows 1002 and 1004, respectively, thereby creating a dome effect. Meanwhile, the lower surface of the bridge 202 formed by the base encapsulation layer 318 may remain pressed flat against a surface, such as a welding table or bench, in order to provide a flat lower surface of the bridge 202 for ultimately being placed in contact with the surface of a patient.

During this welding process, the natural curve in the bridge 202 may be created when the materials of the layers of the bridge 202 are heated and cooled. This melting and cooling process may cause the material of the one or more layers of the bridge 202 to shrink, thereby adding residual stresses into the material in the areas of heating. Such residual stresses in the particular areas of the layers of the bridge 202 welded together may be visually seen as areas of high stress when viewed with a polarization viewing system, according to the principles of photoelasticity.

Figure 11:
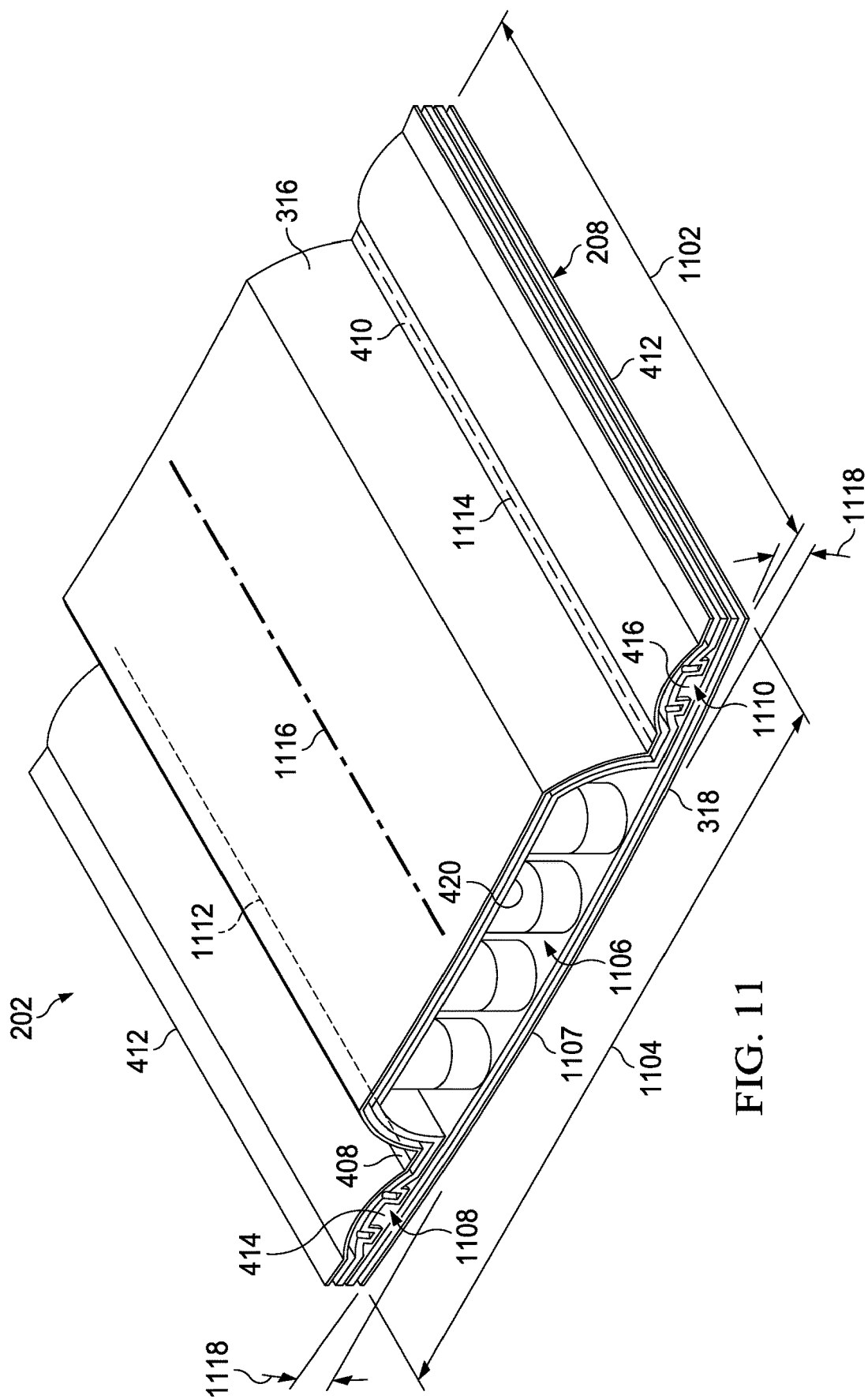
FIG. 11 is a perspective view of a portion of a bridge of a dressing interface, showing additional structural features that may be associated with some example embodiments.

FIG. 11 is a perspective view of a portion of a bridge 202 illustrating some additional details according to some example embodiments. More specifically, FIG. 11 depicts an example section, such as middle section 208, of a bridge 202 that may be curved around multiple hinge points or along multiple hinge lines. For example, the exemplary middle section 208 of FIG. 11 may have a length 1102 and a width 1104, and may comprise curved portions originating from multiple points across the width 1104 of the middle section 208. As shown in FIG. 11, the middle section 208 may include a center section 1106, which may comprise the negative-pressure pathway 420. The center section 1106 may include a first side 1107 formed from a portion of the base encapsulation layer 318 that is substantially flat. The middle section 208 may further include a first curved section 1108 extending along the length 1102 of one edge of the middle section 208, and a second curved section 1110 extending along the length 1102 of a second edge of the middle section 208. The first curved section 1108 and the second curved section 1110 may each include a portion of the base encapsulation layer 318 that has an increasing curvature between the first barrier 408 or second barrier 410, respectively, and the respective adjacent edge of the flange 412. For example, the first curved section 1108 may include the portion of the bridge 202 that spans from a first hinge line 1112 extending along the innermost edge of first barrier 408 to the outer edge of the flange 412 of one side of the bridge 202. Similarly, the second curved section 1110 may include the portion of the bridge 202 that spans from a second hinge line 1114 extending along the innermost edge of second barrier 410 to the outer edge of the flange 412 of a second side of the bridge 202. Each of the first hinge line 1112 and the second hinge line 1114 may extend along the length 1102 of the middle section 208 of the bridge 202 along the edges of weld lines that form the first hinge line 1112 and second hinge line 1114 that are closest to a centerline 1116 of the middle section 208. The first curved section 1108 may include the first sensing pathway 414, while the second curved section 1110 may include the second sensing pathway 416.

While different degrees of curvature of one or more portions of the middle section 208 may be possible, as shown in FIG. 11, the first curved section 1108 and the second curved section 1110 may have approximately the same degree of curvature. For example, as shown in FIG. 11, when the middle section 208 is placed on a flat surface, the center section 1106 of the middle section 208 may lie substantially flat against the flat surface, while the first curved section 1108 and the second curved section 1110 may curve upwards away from the flat surface so that the edges of the flange 412 of each of the curved surfaces are positioned, or deflected, approximately 6 mm above the flat surface, as designated by arrows 1118. In additional or alternative embodiments, the degree of curvature, or deflection, may be greater or less so that the edges of the flange 412 of each of the curved surfaces are positioned in a range between about 1 mm and about 12 mm above the flat surface. In some exemplary embodiments of the bridge 202, only the middle section 208 may include curved portions, while in other embodiments, other portions of the bridge 202, such as the first end 206 and the second end 210, may also comprise one or more curved portions with curved surfaces that project between about 0 mm and about 12 mm above a flat surface.

In operation, the tissue interface 114 may be placed within, over, on, or otherwise proximate a tissue site. The cover 116 may be placed over the tissue interface 114 and sealed to an attachment surface near the tissue site. For example, the cover 116 may be sealed to undamaged epidermis peripheral to a tissue site. Thus, the dressing 104 can provide a sealed therapeutic environment proximate to a tissue site, substantially isolated from the external environment, and the negative-pressure source 102 can reduce the pressure in the sealed therapeutic environment. The dressing interface 118 may be positioned so that the bridge 202 of the dressing interface 118 may be fluidly coupled to the tissue interface 114. For example, the one or more layers of the tissue interface 114 may be fluidly coupled to the recessed space 402 of the first end 206 of the bridge 202. The connector 204 at the second end 210 of the bridge 202 may be fluidly connected to a conduit or tube, such as conduit 212, which may place the dressing interface 118, tissue interface 114, and tissue site in fluid communication with the negative-pressure source 102. Negative pressure may be delivered through the conduit 212 and connector 204 to the second end 210 of the bridge 202 of the dressing interface 118. Negative pressure may then be communicated along the length of the bridge 202 via the negative-pressure pathway 420, and may be delivered to the tissue interface 114 through the opening formed by the one or more apertures in the first end 206 of the bridge 202. Correspondingly, the pressure-sensing pathways, first sensing pathway 414 and second sensing pathway 416, may be in fluid communication with the tissue interface 114 through the first end 206 of the bridge 202 and may communicate pressure measurements to one or more sensors, such as the first sensor 110, and/or the controller 108.

The systems, apparatuses, and methods described herein may provide significant advantages. For example, when applying negative-pressure therapy to a tissue site, such as a wound, it may be advantageous for one or more components of the therapy system 100 to be able to receive feedback of the amount of negative pressure delivered to the tissue site. The therapy system 100 may rely on the feedback pressure measurements to make adjustments to operation of the negative-pressure source 102 and/or other components of the therapy system 100 so as to maintain a consistent therapeutic pressure at the tissue site. The pressure feedback measurements may typically be communicated through pressure-sensing conduits or pathways that are independent from the primary negative-pressure and fluid-removal pathway, such as negative-pressure pathway 420 of the bridge 202. To ensure accurate pressure monitoring and to prevent wound fluid ingress into the pressure-sensing pathways, the one or more pressure-sensing pathways, such as the first sensing pathway 414 and the second sensing pathway 416, may be required to be substantially smaller in diameter than the negative-pressure and fluid-removal pathways. The small width and/or diameter can result in the pressure-sensing pathways being relatively stiff in comparison to the softer and more conformable negative-pressure/fluid-removal pathway. As a result of the relative stiffness of the pressure-sensing pathways, the one or more pressure-sensing pathways could have a potential to develop localized pressure points against the surface of a patient's body.

To alleviate the concern for localized pressure points against the patient's body, the curved shape of the bridge 202 may allow the pressure-sensing pathways to remain out of contact with the skin or surface of the patient, substantially reducing or eliminating localized pressure build-ups along the pressure-sensing pathways. As a result, concerns among caregivers and patients that the potential location of the relatively stiff pressure-sensing pathways may cause localized pressure points may be alleviated. Positioning the pressure-sensing pathways away from being compressed against the surface of a patient's body may also help avoid potential crimping or occlusion, and resulting pressure build-ups within the pressure-sensing pathways. Accordingly, the bridge 202 may provide the features required to provide accurate pressure monitoring of a tissue site to maintain a desired therapeutic pressure level, while also mitigating the risk of localized pressure points due to the inclusion of the pressure-sensing pathways.

The bridge 202 may also provide a smaller total area in contact with the patient, therefore potentially reducing the risk of maceration of healthy skin located underneath the bridge 202. Additionally, curved features of the bridge 202 may be efficiently implemented at a relatively low cost as part of a reel-to-reel manufacturing and assembly protocol.

The systems, apparatuses, and methods described herein may provide further significant advantages. For example, the bridge 202 may provide a substantially flat and low-profile, compressible, and flexible polymeric fluid-management device. The bridge 202 may also be substantially transparent to allow a user to view or inspect conditions within the bridge 202 during the administration of negative-pressure therapy. Additionally, as previously described, some embodiments of the bridge 202 may include attachment or adhesive means, such as a low-tack adhesive, on at least some areas of the patient-facing surfaces of the bridge 202. Using such a low-tack adhesive may ensure that the risk of localized pressure points along the one or more pressure-sensing pathways of the bridge 202 are mitigated by ensuring that the bridge 202 is correctly positioned on the patient. The one or more portions of the bridge 202 comprising a low-tack adhesive may also assist a user during application of the bridge 202 and dressing interface 118 to the patient by providing an additional temporary attachment means, or "third hand." Furthermore, the area of the patient-facing surface of the bridge 202 comprising one or more forms of low-tack adhesive may be sufficiently small so as not to affect the overall transmission of moisture vapor out of the bridge 202.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 104, the container 106, or both may be eliminated or separated from other components for manufacture or sale. In other example configurations, the controller 108 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for managing fluid from a tissue site, comprising:
    a first fluid pathway formed along a length of the apparatus, wherein the first fluid pathway comprises a first plurality of bubbles;
    a second fluid pathway formed along the length of the apparatus; and
    a third fluid pathway formed along the length of the apparatus;
    wherein the apparatus has a width, and further comprises a first section, a second section, and a third section across the width, wherein the first fluid pathway is in the first section, the second fluid pathway, is in the second section, and the third fluid pathway is in the third section, and wherein the first section comprises a flat face and the second section is adapted to curve away from the flat face.

2. The apparatus of claim 1, wherein the third section is adapted to curve away from the flat face.

3. The apparatus of claim 1, further comprising a first barrier formed along the length of the apparatus between the first fluid pathway and the second fluid pathway.

4. The apparatus of claim 3, further comprising a second barrier formed along the length of the apparatus between the first fluid pathway and the third fluid pathway.

5. The apparatus of claim 1, wherein the first fluid pathway is formed in a sealed space between a first layer and a second layer of the apparatus.

6. The apparatus of claim 1, further comprising a second plurality of bubbles disposed within the second fluid pathway and the third fluid pathway.

7. The apparatus of claim 1, further comprising a first port at a first end of the apparatus, wherein the first port is in fluid communication with the first fluid pathway and configured to be in fluid communication with the tissue site.

8. The apparatus of claim 7, further comprising a second port at a second end of the apparatus, wherein the second port is adapted to be fluidly coupled between the first fluid pathway and a negative-pressure source.

9. The apparatus of claim 1, further comprising an adhesive on a patient-facing surface of the apparatus.

10. The apparatus of claim 9, wherein the adhesive is configured to mitigate the risk of localized pressure points on a patient by indicating the correct position of the apparatus with respect to the patient.

* * * * *

UNITED STATES PATENT AND TRADEMARK OFFICE
CERTIFICATE OF CORRECTION

PATENT NO. : 11,534,343 B2  
APPLICATION NO. : 16/449750  
DATED : December 27, 2022  
INVENTOR(S) : Thomas Alan Edwards Page 1 of 1

It is certified that error appears in the above-identified patent and that said Letters Patent is hereby corrected as shown below:

In the Claims

Column 26
Line 22, In Claim 1, between "the second fluid pathway" and "is in the" delete ",".

Signed and Sealed this
Ninth Day of April, 2024

Katherine Kelly Vidal
*Director of the United States Patent and Trademark Office*